United States Patent [19]

Kazmierczak et al.

[11] Patent Number: 4,801,749

[45] Date of Patent: Jan. 31, 1989

[54] PHENOLIC ANTIOXIDANT HYDRAZIDES

[75] Inventors: Robert T. Kazmierczak; Ronald E. MacLeay; Jerome Wicher, all of Erie, N.Y.

[73] Assignee: Pennwalt Corporation, Philadelphia, Pa.

[21] Appl. No.: 84,536

[22] Filed: Aug. 12, 1987

[51] Int. Cl.$^4$ .................. C07C 103/20; C07C 103/29
[52] U.S. Cl. ..................................... 564/158; 564/150; 260/404.5
[58] Field of Search ................. 260/404.5 H, 404.5 R; 564/34, 35, 150, 158

[56] References Cited

U.S. PATENT DOCUMENTS

| | | | |
|---|---|---|---|
| 3,282,939 | 11/1966 | Spivack et al. | 260/404.5 |
| 3,660,438 | 5/1972 | Dexter | 260/404.5 |
| 3,699,053 | 10/1972 | Gentit | 260/404.5 |
| 3,856,748 | 12/1974 | Dexter et al. | 564/158 |

Primary Examiner—H. M. S. Sneed
Assistant Examiner—Elizabeth Irzinski
Attorney, Agent, or Firm—Panitch Schwarze Jacobs & Nadel

[57] ABSTRACT

Phenolic antioxidant hydrazides are provided which are useful to stabilize organic materials (such as synthetic polymers) which are subject to oxidative degradation.

6 Claims, No Drawings

PHENOLIC ANTIOXIDANT HYDRAZIDES

BACKGROUND OF THE INVENTION

This invention relates to phenolic antioxidant hydrazide compounds useful as stabilizers for organic materials subject to thermooxidative degradation, including a large variety of synthetic polymers.

When plastic materials are exposed to a high temperature environment either in processing or in final application, degradation generally occurs as evidenced by discoloration, cracking, and loss of mechanical properties. To help overcome these effects a great number of heat stabilizer additives are commercially available. Polymers may be protected against themooxidative degradation by the use of a chain breaking antioxidant additive. The chain breaking type of stabilizer intercepts the propagation step in the oxidative degradation mechanism and thereby reduces the overall oxidation rate. Hindered phenols are one example of this kind of antioxidant.

Another way to inhibit thermal degradation is to use a metal deactivator additive. Transition metals such as copper, iron, cobalt and manganese are known to greatly accelerate the rate of oxidation by catalyzing the decomposition of hydroperoxides to radical species (*Encyclopedia of Polymer Science and Engineering*, John Wiley & Sons, New York, New York, 1985, Vol 2, p 75). A metal deactivator will complex with such metals (or ions) to block their catalytic activity. Derivatives of oxamide and hydrazine are generally the types of compounds used commercially as deactivators.

Oxamide phenols have long been known as effective antioxidant stabilizers. U.S. Pat. Nos. 3,706,798 and 3,734,884 disclose reacting hindered phenol oxamide esters with diamines to give bisoxalic acid diamides. These materials are stabilizers for polypropylene. U.S. Pat. No. 4,145,556 discloses the use of N,N'-bis[(alkylhydroxyphenyl)alkanoylhydrocarbyl]oxamides as stabilizers for polyolefins against degradation from thermal as well as metal catalyzed oxidation. U.S. Pat. No. 3,894,083 discloses that oxamic acid hydrazones are useful as antioxidants for many types of polymeric materials such as polyolefins, acrylates, acrylonitrile and ABS blends. U.S. Pat. No. 4,012,360 discloses bis salicyloyl oxalic acid dihydrazides as effective cobalt and manganese deactivators in polypropylene. U.S. Pat. No. 4,073,771 discloses that condensation of oxalyl dihydrazide with hindered phenol aldehydes and ketones provide both effective thermal antioxidants and stabilizers which provide protection to polymers (polyethylene) against the effects of active metals (e.g., copper), known to accelerate thermal oxidation. U.S. Pat. No. 4,304,714 discloses preparing multiphenolic antioxidant compounds from hydroxymethyl oxamides and hindered phenol propionate esters or acid chlorides for use as thermal antioxidants for polypropylene.

Thermal stabilization of polymers through metal complexation has also been shown for compounds other than the oxamide derivatives. Reaction products of o-hydroxy aromatic carbonyl compounds with alkyl diamines are effective metal deactivators (R. L. Hartless, A. M. Trozzolo, Synthesis and Evaluation of New Stabilizers for Polyethylene Insulation, Am. Chem. Soc., Div. Org. Coat. Plast. Chem., Pap. 1974, 34(2), 177–84 (Eng)). U.S. Pat. No. 4,038,247 discloses that diacyl dihydrazides are particularly effective for stabilizing polyolefins against metal catalyzed oxidation. U.S. Pat. No. 3,870,680 discloses the use of diacyl hydrazines in conjunction with hindered phenols to stabilize polyolefins against copper-catalyzed thermal degradation. U.S. Pat. No. 4,147,689 discloses reacting hindered phenol substrates with thiodicarboxylic acid dihydrazides to provide primary antioxidant, secondary antioxidant, and metal deactivation functions in a single compound.

Oxamide hydrazones, prepared by condensing oxalyl dihydrazide with o-hydroxy aryl carbonyl compounds, combine two known metal deactivating functions and were used to stabilize polyethylene cable insulation (R. L. Hartless, A. M. Trozzolo, Syntheseis and Evaluation of New Stabilizers for Polyethylene Insulation, Am. Chem. Soc., Div. Org. Coat. Plast. Chem., Pap. 1974, 34(2), 177–84 (Eng)).

SUMMARY OF THE INVENTION

The present invention is directed to a compound having the formula:

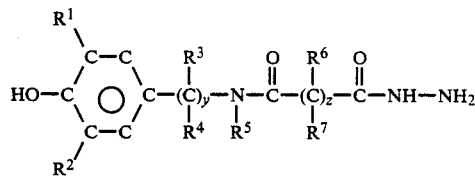

wherein
$R^1$ is t-alkyl of 4 to 8 carbons,
$R^2$ is selected from hydrogen, t-alkyl of 4 to 8 carbons, and alkyl of 1 to 8 carbons,
$R^3$, $R^4$, $R^5$, $R^6$, and $R^7$ are independently selected from hydrogen, lower alkyl of 1 to 6 carbons, and phenyl,
y is an integer of from 0 to 6, and
z is an integer of from 0 to 10.

Preferably, $R^1$ is a t-alkyl of 4 or 5 carbons, $R^2$ is selected from t-alkyl of 4 to 6 carbons and alkyl of 1 to 5 carbons, $R^3$, $R^4$, $R^5$, $R^6$, and $R^7$ are independently selected from hydrogen and alkyl of 1 to 5 carbons, y is an integer of from 0 to 4, and z is an integer of from 0 to 6. Most preferably, $R^1$ and $R^2$ are t-butyl, $R^3$, $R^4$, $R^5$, $R^6$, and $R^7$ are hydrogen, y is an integer of from 0 to 3, and z is an integer of from 0 to 2.

DETAILED DESCRIPTION OF THE INVENTIONS

The invention provides a series of phenolic hydrazide stabilizers prepared from phenolic substituted carboxylic acid esters and hydrazine. The stabilizers may be used alone or reacted as intermediates with anhydride copolymers to prepare non-fugitive, high molecular weight antioxidant compositions.

Representative examples of the phenolic hydrazide of this invention are as follows:

1. 2-(3,5-di-t-amyl-4-hydroxyphenylamino)-2-oxoacetyl hydrazide,
2. 2-(3,5-di-t-hexyl-4-hydroxyphenylamino)-2-oxoacetyl hydrazide,
3. 2-(3-t-butyl-5-methyl-4-hydroxyphenylamino)-2-oxoacetyl hydrazide,
4. 2-(3-t-amyl-5-methyl-4-hydroxyphenylamino)-2-oxoacetyl hydrazide,
5. 2-(3,5-di-t-butyl-4-hydroxybenzylamino)-2-oxoacetyl hydrazide, 6. 2-(3,5-di-t-amyl-4-hydroxybenzylamino)-2-oxoacetyl hydrazide,
7. 2-(3-t-butyl-5-ethyl-4-hydroxybenzylamino)-2-oxoacetyl hydrazide,
8. 2-(2-(3,5-di-t-butyl-4-hydroxyphenyl)ethylamino)-2-oxoacetyl hydrazide,
9. 2-(3-(3,5-di-t-amyl-4-hydroxyphenyl)propylamino)-2-oxoacetyl hydrazide,
10. 2-(4-(3,5-di-t-butyl-4-hydroxyphenyl)butylamino)-2-oxoacetyl hydrazide,
11. 2-(1-(3,5-di-t-butyl-4-hydroxybenzyl)propylamino)-2-oxoacetyl hydrazide,
12. 2-(2-(3,5-di-t-butyl-4-hydroxyphenyl)butylamino)-2-oxoacetyl hydrazide,
13. 2-(3,5-di-t-butyl-4hydroxybenzylmethyl)amino-2-oxoacetyl hydrazide,
14. 2-(3-t-butyl-5-methyl-4-hydroxybenzylethyl)amino-2-oxoacetyl hydrazide,
15. 4-(3,5-di-t-butyl-4-hydroxyphenyl-amino)-4-oxobutanoyl hydrazide,
16. 6-(3,5-di-t-butyl-4-hydroxyphenylamino-6-oxohexanoyl hydrazide, and
17. 10-(3,5-di-t-butyl-4-hydroxy-phenylamino)-10-oxodecanoyl hydrazide.

Examples of such polymers and copolymers which may be stabilized by these compounds include:
1. Polyolefins such as high, low and linear low density polyethylenes, which may be optionally crosslinked, polypropylene, polyisobutylene, poly(methylbutene-1), polyacetylene and in general polyolefins derived from monomers having from two to about ten carbons and mixtures thereof.
2. Polyolefins derived from diolefins such as polybutadiene and polyisoprene.
3. Copolymers of mono or diolefins such as ethylene-propylene, propylene-butene-1, propylene-isobutylene and ethylene-butene-1 copolymers.
4. Terpolymers of ethylene and propylene with dienes (EPDM) such as butadiene, hexadiene, dicyclopentadiene and ethylidene norbornene.
5. Copolymers of alpha-olefins with acrylic acid or methacrylic acids or their derivatives such as ethylene-acrylic acid, ethylene-methacrylic acid and ethylene-ethyl acrylate copolymers.
6. Styrenic polymers such as polystyrene (PS) and poly(p-methylstyrene).
7. Styrenic copolymers and terpolymers such as styrene-butadiene (SBR), styrene-allyl alcohol and styrene-acrylonitrile (SAN), Styrene-acrylonitrile-methacrylate terpolymer, styrene-butadiene-styrene block copolymers (SBS), rubber modified styrenics such as styrene-acrylonitrile copolymers modified with acrylic ester polymer (ASA), graft copolymers of styrene on rubbers such as polybutadiene (HIPS), polyisoprene or styrene-butadiene-styrene block copolymers, graft copolymers of styrene-acrylonitrile on rubbers such as butadiene (ABS), polyisoprene or styrene-butadiene-styrene block copolymers, graft copolymers of styrene-methyl methacrylate on rubbers such as polybutadiene (MBS), butadiene-styrene radial block copolymers (e.g., KRO 3 of Phillips Petroleum Co.), selectively hydrogenated butadiene-styrene block copolymers (e.g. Kraton G. from Shell Chemical Co.) and mixtures thereof.
8. Polymers and copolymers derived from halogen-containing vinyl monomers such as poly(vinyl chloride), poly(vinyl fluoride), poly(viylidene chloride), poly(vinylidene fluoride), poly(tetrafluoroethylene) (PTFE), vinyl chloride-vinyl acetate copolymers, vinylidene chloride-vinyl acetate copolymers and ethylene-tetrafluoroethylene copolymers.
9. Halogenated rubbers such as chlorinated and/or brominated butyl rubbers and fluoroelastomers.
10. Polymers and copolymers derived from alpha, beta-unsaturated acids, anhydrides, ester, amides and nitriles or combinations thereof such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the above polymers and various blends and mixtures thereof as well as rubber modified versions of the above polymers and copolymers.
11. Polymers and copolymers derived from unsaturated alcohols or their acylated derivative such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ACC), ethylene-vinyl acetate copolymer, and ethylene-vinyl alcohol copolymers.
12. Polymers and copolymers derived from unsaturated amines such as poly(allyl melamine).
13. Polymers and copolymers derived from epoxides such as polyethylene oxide, polypropylene oxide and copolymers thereof as well as polymers derived from bis-glycidyl ethers.
14. Poly(phenylene oxides), poly(phenylene ethers) and modifications thereof containing grafted polystyrene or rubbers as well as their various blends with polystyrene, rubber modified polystyrenes or nylon.
15. Polycarbonates and especially the aromatic polycarbonates such as those derived from phosgene and bisphenols such as biphenol-A, tetrabromobisphenol-A and tetramethylbisphenol-A.
16. Polyester derived from dicarboxylic acids and diols and/or hydroxycarboxylic acids or their corresponding lactones such as polyalkylene phthalates (e.g., polyethylene terephthalate (PET), polybutylene terephthalate (PBT), and poly(1,4-dimethylcyclohexane terephthalate) or copolymers thereof) and polylactones such as polycaprolactone.
17. Polyacrylates derived from bisphenols (e.g., bisphenol-A) and various aromatic acids such as isophthalic and terephthalic acids or mixtures thereof.
18. Aromatic copolyestercarbonates having carbonate as well as ester inkages present in the backbone of the polymers such as those derived from bisphenols, iso- and terephthaloyl chlorides and phosgene.
19. Polyurethanes and polyureas.
20. Polyacetals such as polyoxymethylenes and polyoxymethylenes which contain ethylene oxide as a comonomer.
21. Polysulfones, polyethersulfones and polyimidesulfones.
22. Polyamides and copolyamides which are derived from diamines and dicarboxylic acids and/or from aminocarboxylic acids or the corresponding lactams such as the following nylons: 6, 6/6, 6/10, 11, and 12.
23. Polyimides, polyetherimides, polyamideimides and copolyetheresters.
24. Cross-linked polymers which are derived from aldehydes on the one hand and from phenols, ureas and melamine on the other hand such as phenol-formaldehyde, urea-formaldehyde and melamine-formaldehyde resins.

25. Alkyl resins such as glycerol-phthalic acid resins and mixtures thereof with melamine-formaldehyde resins.
26. Unsaturated polyester resins which are derived from copolyesters of saturated and unsaturated dicarboxylic acids with polyhydric alcohols as well as from vinyl compounds (crosslinking agents) and also halogen-containing, flame resistant modifications thereof.
27. Natural polymers such as cellulose, natural rubber as well as the chemically modified homologous derivatives thereof such as cellulose acetates, cellulose propionate, cellulose butyrate and the cellulose ethers such as methyl and ethyl cellulose.

In addition the stabilizers of this invention may be used to stabilize various combinations or blends of the above polymers or copolymers. Use levels for the stabilizers of this invention range from 0.01 to 5% by weight of the composition, preferably between 0.1% and 2%. Additionally, the reactive stabilizers of this invention are useful in preparing non-fugitive, high molecular weight antioxidant compositions. The stabilizers of this invention are readily attached to a multitude of anhydride copolymers through an imide linkage to prepare such compositions.

The stabilizers of this invention are prepared by reacting aminophenols or aminoalkyl phenols of general formula A

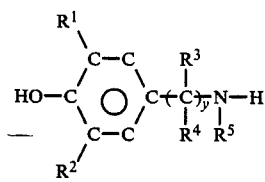

wherein $R^1$, $R^2$, $R^3$, $R^4$, $R^5$ and y are as previously defined, with alkyl halooxoalkanoates and, optionally, a condensation catalyst to form intermediate phenolic substituted alkyl esters of structure B

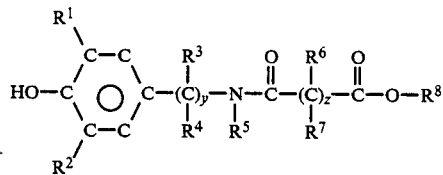

where $R^8$ is alkyl of 1 to 6 carbons and $R^1$ through $R^7$, y and z are as previously defined.

Alternatively, the ester intermediates B are prepared by reacting phenols of general structure A with dioic acid diesters of general structure C

where $R^8$ and z are as previously defined.

Examples of amino substituted hindered phenols (A) used as intermediates for ester preparation include the following:
2,6-di-t-butyl-4-aminophenol,
2,6-di-t-amyl-4-aminophenol,
2,6-di-t-hexyl-4-aminophenol,
2-t-butyl-6-methyl-4-aminophenol,
2-t-amyl-6-methyl-4-aminophenol,
3,5-di-t-butyl-4-hydroxybenzylamine,
3,5-di-t-amyl-4-hydroxybenzylamine,
2-(3,5-di-t-butyl-4-hydroxyphenyl)ethylamine,
3-(3,5-di-t-butyl-4-hydroxyphenyl)propylamine,
4-(4-aminobutyl)-2,6-di-t-butylphenol,
4-(2-aminobutyl)-2,6-di-t-butylphenol,
4-(1-(aminomethyl)propyl)-2,6-di-t-butylphenol,
3,5-di-t-butyl-4-hydroxybenzylmethylamine, and
3-t-amyl-5-methyl-4-hydroxybenzylethylamine.

Examples of alkyl halooxoalkanoates used to prepare ester intermediates B include the following:
ethyl chlorooxoacetate, ethyl 4-chloro-4-oxobutanoate, ethyl bromooxoacetate, methyl chlorooxoacetate, ethyl 4-bromo-4-oxobutanoate, methyl 4-bromo-4-oxobutanoate, methyl bromooxoacetate, and ethyl 6-chloro-6-oxohexanoate.

Examples of diesters used to prepare ester intermediates B include the following:
dimethyl oxalate, diethyl oxalate, dimethyl malonate, dimethyl succinate, and dimethyl adipate.

Suitable solvents for the preparation of B include aromatic hydrocarbons, halogenated aromatic hydrocarbons, haloalkanes, or ethers (eg., toluene, chlorobenzene, methylene chloride diethyl ether, and dioxane). Preferred condensation catalysts are tertiary amines such as trialkylamines or pyridine.

The condensation according to the above described reaction is performed at temperatures between 0° C. and 150° C. depending on the reactivity of the phenolic substrate A. Preferably, the reactions are carried out at temperatures between 0° C. and 60° C.

Intermediate esters (B) are subsequently reacted with excess hydrazine hydrate in alcoholic media between 0° C. and 150° C. to form the stabilizers of the invention. The hydrazinolysis is preferably performed with the lower alcohols (of 1 to 4 carbons) as solvents at temperatures near the boiling point of said alcohols. Dilution of the reaction mixture with water generally precipitates the product which may be collected by filtration.

EXAMPLE 1

Preparation of 2-(3,5-di-t-butyl-4-hydroxyphenylamino)-2-oxoacetyl hydrazide

An amount of 6.4 g (0.02 mole) of ethyl 2-(3,5-di-t-butyl-4-hydroxyphenylamino)-2-oxoacetate was slurried with 20 ml of ethanol. Hydrazine hydrate (7.1 g, 85%, 0.12 mole) was then added dropwise over a 5 minute period at a temperature of between 23° and 30° C. The mixture was stirred for 30 minutes at ambient temperature, then refluxed gently for 3 hours. The solution was cooled to 50° C. and poured into 350 ml of water. The resultant slurry was chilled to 10° C. before collecting the solids by filtration. After drying, the solids were recrystallized from methylene chloride and hexane to give 2.8 g (45.5%) of white solids, MP 199°–206° C. IR: 1685 cm$^{-1}$ (C=O), 3640 cm$^{-1}$ (OH), 3360 and 3430 cm$^{-1}$ (NH).

EXAMPLE 2

Preparation of 2-(3-(3,5-di-t-butyl-4-hydroxyphenyl)propylamino)-2-oxoacetyl hydrazide An amount of 0.74 g (0.002 mole) of ethyl 2-(3,5-di-t-butyl-4-hydroxyphenyl)propylamino)-2-oxoacetate was dissolved in 5 ml of methanol. To this was added, by pipet, 0.60 g (0.010 mole) of 85% hydrazine hydrate dissolved in 5 ml of methanol. The solution was stirred at room temperature under a nitrogen atmosphere for 30 minutes followed by reflux for 20 minutes. The reaction mixture was cooled and pipetted dropwise into 75 ml of rapidly stirred water. A white precipitate that formed was collected by vacuum filtration and dried under high vacuum for several hours. There was obtained 0.65 g of chalky white solids, MP 102–107. IR: 1660 cm$^{-1}$ (C=O), 3640 cm$^{-1}$ (OH), 3300 cm$^{-1}$ (NH). Elemental Anal: C 65.32, H 8.92, N 11.79, O 13.70. Calc: C 65.30, H 8.94, N 12.02, O 13.73.

EXAMPLE 3

Preparation of 4-(3,5-di-t-butyl-4-hydroxyphenylamino)-4-oxobutanoyl hydrazide

An amount of 1.25 g (0.003 mole) of ethyl 4-(3,5-di-t-butyl-4-hydroxyphenylamino)-4-oxobutanoate was dissolved in 5 ml of methanol. To this was added, by pipet, 1.06 g (0.018 mole) of 85% hydrazine hydrate dissolved in 5 ml of methanol. The solution was stirred at room temperature under a nitrogen atmosphere for one hour, allowed to stand overnight, and then refluxed for 1 hour. The mixture was cooled and poured into 100 ml of stirred water. The precipitate was collected by vacuum filtration and dried by azeotropic distillation with excess toluene. The resultant toluene slurry was chilled in an ice bath prior to collection of the solids by vacuum filtration. A 10 ml toluene rinse removed traces of color from the solids. After high vacuum drying there remained 0.89 g of white crystalline solids, M.P. 226° C. (dec.). IR: 1640 cm$^{-1}$ (C=O), 3270 cm$^{-1}$ (NH$_2$).

Elemental Anal.: C 64.43, H 8.54, N 12.44, O 14.17, Calc.: C 64.45, H 8.71, N 12.53, O 14.31.

What is claimed:
1. A compound having the formula

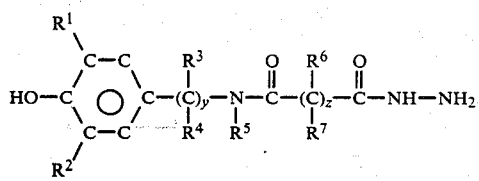

wherein
R$^1$ is a tertiary alkyl of 4 to 8 carbons,
R$^2$ is selected from hydrogen, t-alkyl of 4 to 8 carbons, and alkyl of 1 to 8 carbons,
R$^3$, R$^4$, R$^5$, R$^6$, and R$^7$ are independently selected from hydrogen, alkyl of 1 to 6 carbons, and phenyl,
y is an integer of from 0 to 6, and
z in an integer of from 0 to 10.

2. The compound of claim 1 wherein R$^1$ is t-alkyl of 4 to 5 carbons, R$^2$ is selected from t-alkyl of 4 to 6 carbons and alkyl of 1 to 5 carbons, R$^3$, R$^4$, R$^5$, R$^6$, and R$^7$ are independently selected from alkyl of 1 to 5 carbons and hydrogen, y is an integer of from 0 to 4, and z is an integer from 0 to 6.

3. The compound of claim 2 wherein R$^1$ and R$^2$ are t-butyl, R$^3$, R$^4$, R$^5$, R$^6$ and R$^7$ are hydrogen, y is an integer of from 0 to 3 and z is an integer of from 0 to 2.

4. The compound of claim 3 is 2-(3,5-di-t-butyl-4-hydroxyphenylamino)-2-oxoacetyl hydrazide.

5. A compound of claim 3 is 2-(3(3,5-di-t-butyl-4-hydroxyphenyl)propyl-amino)-2-oxoacetyl hydrazide.

6. A compound of claim 3 is 4-(3,5-di-t-butyl-4-hydroxyphenylamino)-4-oxobutanoyl hydrazide.

* * * * *